US 12,161,795 B2

(12) United States Patent
Rapp et al.

(10) Patent No.: US 12,161,795 B2
(45) Date of Patent: Dec. 10, 2024

(54) SMALL STEP SIZE AND HIGH RESOLUTION AEROSOL GENERATION SYSTEM AND METHOD

(71) Applicant: Pneuma Respiratory, Inc., Boone, NC (US)

(72) Inventors: Gregory Rapp, Boone, NC (US); Jeffrey Miller, Boone, NC (US); Shi-Bo Wang, Shenzhen (CN); Judson Sidney Clements, Boone, NC (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 0 days.

(21) Appl. No.: 18/354,373

(22) Filed: Jul. 18, 2023

(65) Prior Publication Data
US 2024/0017023 A1    Jan. 18, 2024

Related U.S. Application Data

(60) Provisional application No. 63/390,209, filed on Jul. 18, 2022.

(51) Int. Cl.
*A61M 11/00* (2006.01)
(52) U.S. Cl.
CPC .................. *A61M 11/005* (2013.01)
(58) Field of Classification Search
CPC .......... A61M 11/005; A61M 11/001; A61M 15/001; A61M 15/0005; A61M 15/0085; B05B 17/06; B05B 17/0607; B05B 17/0615; B05B 17/0623; B05B 17/063;
(Continued)

(56) References Cited

U.S. PATENT DOCUMENTS

| 3,934,585 A | 1/1976 | Maurice |
| 3,970,250 A | 7/1976 | Drews |
| 5,021,701 A | 6/1991 | Takahashi et al. |

(Continued)

FOREIGN PATENT DOCUMENTS

| AU | 2012258488 | 1/2013 |
| CA | 2364248 | 8/2006 |

(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.

(Continued)

*Primary Examiner* — Joseph D. Boecker
*Assistant Examiner* — Brian T Khong
(74) *Attorney, Agent, or Firm* — Polsinelli PC

(57) ABSTRACT

An aerosol generation device includes a circuit or microcontroller for automatically detecting and adjusting vibration frequency of an electronic transducer to a determined resonance frequency that changes during operation of the device whereby the circuit or microcontroller provides a plurality of tuning signal waves at each of a plurality of time intervals during operation of the electronic transducer from comparison of the current measured for each signal wave during each time interval.

19 Claims, 5 Drawing Sheets

(58) Field of Classification Search
CPC ............ B05B 17/0638; B05B 17/0646; B05B 17/0653; B05B 17/0661; B05B 17/0669
See application file for complete search history.

(56) References Cited

U.S. PATENT DOCUMENTS

| | | | |
|---|---|---|---|
| 5,164,740 A | 11/1992 | Ivri | |
| 5,239,993 A | 8/1993 | Evans | |
| 5,312,281 A | 5/1994 | Takahashi et al. | |
| 5,363,842 A | 11/1994 | Mishelevich et al. | |
| 5,487,378 A | 1/1996 | Robertson et al. | |
| 5,497,763 A | 3/1996 | Lloyd et al. | |
| 5,586,550 A | 12/1996 | Ivri et al. | |
| 5,607,410 A | 3/1997 | Branch | |
| 5,630,793 A | 5/1997 | Rowe | |
| 5,724,959 A | 3/1998 | McAughey et al. | |
| 5,758,637 A | 6/1998 | Ivri et al. | |
| 5,826,570 A | 10/1998 | Goodman et al. | |
| 5,828,394 A | 10/1998 | Khuri-Yakub et al. | |
| 5,881,716 A | 3/1999 | Wirch et al. | |
| 5,884,620 A | 3/1999 | Gonda et al. | |
| 5,894,841 A | 4/1999 | Voges | |
| 5,906,202 A | 5/1999 | Schuster et al. | |
| 5,938,117 A | 8/1999 | Ivri | |
| 5,979,247 A | 11/1999 | Kizawa | |
| 6,011,062 A | 1/2000 | Schneider et al. | |
| 6,026,809 A | 2/2000 | Abrams et al. | |
| 6,062,212 A | 5/2000 | Davison et al. | |
| 6,071,498 A | 6/2000 | Narodylo et al. | |
| 6,085,740 A | 7/2000 | Ivri et al. | |
| 6,158,431 A | 12/2000 | Poole | |
| 6,196,219 B1 | 3/2001 | Hess et al. | |
| 6,235,177 B1 | 5/2001 | Borland et al. | |
| 6,358,058 B1 | 3/2002 | Strupat et al. | |
| 6,443,146 B1 | 9/2002 | Voges | |
| 6,511,718 B1 | 1/2003 | Paz de Araujo et al. | |
| 6,523,762 B1 | 2/2003 | Luginbuhl et al. | |
| 6,539,937 B1 | 4/2003 | Haveri | |
| 6,546,927 B2 | 4/2003 | Litherland et al. | |
| 6,615,826 B1 | 9/2003 | Gabrio et al. | |
| 6,629,524 B1 | 10/2003 | Goodall et al. | |
| 6,637,430 B1 | 10/2003 | Voges et al. | |
| 6,896,910 B2 | 5/2005 | Kim et al. | |
| 6,930,861 B2 | 8/2005 | Huha et al. | |
| 6,978,941 B2 | 12/2005 | Litherland et al. | |
| 6,981,499 B2 | 1/2006 | Anderson et al. | |
| 7,131,599 B2 | 11/2006 | Katase | |
| 7,191,777 B2 | 3/2007 | Brand et al. | |
| 7,198,044 B2 | 4/2007 | Trueba | |
| 7,219,664 B2 | 5/2007 | Ruckdeschel et al. | |
| 7,628,339 B2 | 12/2009 | Ivri et al. | |
| 7,648,957 B2 | 1/2010 | Heyden et al. | |
| 7,708,011 B2 | 5/2010 | Hochrainer et al. | |
| 7,883,031 B2 | 2/2011 | Collins, Jr. et al. | |
| 7,900,625 B2 | 3/2011 | Kleinstreuer et al. | |
| 7,954,486 B2 | 6/2011 | Papania et al. | |
| 7,976,140 B2 | 7/2011 | Umeda | |
| 8,012,136 B2 | 9/2011 | Collins, Jr. et al. | |
| 8,367,734 B1 | 2/2013 | Gao et al. | |
| 8,474,452 B2 | 7/2013 | Gumaste et al. | |
| 8,545,463 B2 | 10/2013 | Collins, Jr. et al. | |
| 8,555,874 B2 | 10/2013 | Fink et al. | |
| 8,616,195 B2 | 12/2013 | Power et al. | |
| 8,684,980 B2 | 4/2014 | Hunter et al. | |
| 8,733,935 B2 | 5/2014 | Ballou, Jr. et al. | |
| 8,753,308 B2 | 6/2014 | Palmer et al. | |
| 8,936,021 B2 | 1/2015 | Collins, Jr. | |
| 8,985,100 B2 | 3/2015 | Minocchieri et al. | |
| 9,022,027 B2 | 5/2015 | Addington et al. | |
| 9,087,145 B2 | 7/2015 | Ballou, Jr. et al. | |
| 9,227,029 B2 | 1/2016 | Addington et al. | |
| 9,242,054 B2 | 1/2016 | Fink et al. | |
| 9,352,108 B1 | 5/2016 | Reed et al. | |
| 9,452,274 B2 | 9/2016 | Addington et al. | |
| 9,463,486 B2 | 10/2016 | Wilkerson et al. | |
| 9,539,604 B2 | 1/2017 | Wilkerson et al. | |
| 9,757,528 B2 | 9/2017 | Rubin | |
| 9,956,360 B2 | 5/2018 | Germinario et al. | |
| 9,962,507 B2 | 5/2018 | Germinario et al. | |
| 10,449,314 B2 | 10/2019 | Germinario et al. | |
| 10,525,220 B2 | 1/2020 | Hunter et al. | |
| 10,568,543 B2 | 2/2020 | Yan | |
| 10,857,310 B2 | 12/2020 | Muellinger et al. | |
| 10,898,666 B2 | 1/2021 | Germinario et al. | |
| 2002/0002975 A1 | 1/2002 | Power | |
| 2002/0032387 A1 | 3/2002 | Geva et al. | |
| 2002/0046750 A1 | 4/2002 | Gonda et al. | |
| 2002/0071871 A1 | 6/2002 | Snyder et al. | |
| 2002/0077369 A1 | 6/2002 | Noolandi et al. | |
| 2002/0121274 A1 | 9/2002 | Borland et al. | |
| 2002/0129813 A1* | 9/2002 | Litherland ............ H10N 30/802 128/200.16 |
| 2003/0062042 A1 | 4/2003 | Wensley et al. | |
| 2003/0072717 A1 | 4/2003 | Reinhold et al. | |
| 2003/0098022 A1 | 5/2003 | Nakao et al. | |
| 2003/0101991 A1 | 6/2003 | Trueba | |
| 2003/0127538 A1 | 7/2003 | Patel et al. | |
| 2003/0140921 A1 | 7/2003 | Smith et al. | |
| 2003/0150445 A1 | 8/2003 | Power et al. | |
| 2003/0196654 A1 | 10/2003 | Stein | |
| 2003/0205229 A1 | 11/2003 | Crockford et al. | |
| 2004/0009231 A1 | 1/2004 | Jackson et al. | |
| 2004/0045547 A1 | 3/2004 | Yamamoto et al. | |
| 2004/0084044 A1 | 5/2004 | Childers et al. | |
| 2004/0139963 A1 | 7/2004 | Ivri et al. | |
| 2004/0195403 A1 | 10/2004 | Atterybury et al. | |
| 2004/0215157 A1 | 10/2004 | Peclat et al. | |
| 2004/0256487 A1 | 12/2004 | Collins, Jr. et al. | |
| 2005/0011514 A1 | 1/2005 | Power et al. | |
| 2005/0077315 A1 | 4/2005 | Pavlu et al. | |
| 2005/0121025 A1 | 6/2005 | Gamard et al. | |
| 2005/0150489 A1 | 7/2005 | Dunfield et al. | |
| 2005/0166912 A1 | 8/2005 | Sexton et al. | |
| 2005/0172476 A1 | 8/2005 | Stone et al. | |
| 2005/0172958 A1 | 8/2005 | Singer et al. | |
| 2005/0217666 A1 | 10/2005 | Power | |
| 2005/0224075 A1 | 10/2005 | Childers et al. | |
| 2005/0224076 A1 | 10/2005 | Pfichner et al. | |
| 2005/0236501 A1 | 10/2005 | Zimlich, Jr. et al. | |
| 2006/0243274 A1* | 11/2006 | Lieberman ............ A61M 11/005 128/200.14 |
| 2007/0023036 A1 | 2/2007 | Grychowski et al. | |
| 2007/0044793 A1 | 3/2007 | Kleinstreuer et al. | |
| 2007/0062520 A1 | 3/2007 | Nobutani et al. | |
| 2007/0083677 A1 | 4/2007 | Cecka et al. | |
| 2007/0119968 A1 | 5/2007 | Collins, Jr. et al. | |
| 2007/0119969 A1 | 5/2007 | Collins, Jr. et al. | |
| 2007/0125370 A1 | 6/2007 | Denyer et al. | |
| 2007/0157931 A1 | 7/2007 | Parker et al. | |
| 2007/0240714 A1 | 10/2007 | Dunne et al. | |
| 2007/0248645 A1 | 10/2007 | Bague et al. | |
| 2007/0267010 A1 | 11/2007 | Fink et al. | |
| 2008/0000470 A1 | 1/2008 | Minocchieri et al. | |
| 2008/0059228 A1 | 3/2008 | Bossi et al. | |
| 2008/0142010 A1 | 6/2008 | Weaver et al. | |
| 2008/0243050 A1 | 10/2008 | Power et al. | |
| 2008/0271732 A1 | 11/2008 | Weaver et al. | |
| 2008/0283049 A1 | 11/2008 | Mahoney et al. | |
| 2008/0283057 A1 | 11/2008 | Rohrschneider et al. | |
| 2008/0295827 A1 | 12/2008 | Kobayashi | |
| 2008/0308096 A1 | 12/2008 | Borgschulte et al. | |
| 2009/0038610 A1 | 2/2009 | Bogh et al. | |
| 2009/0093772 A1 | 4/2009 | Genosar et al. | |
| 2009/0101144 A1 | 4/2009 | Gamard et al. | |
| 2009/0107492 A1 | 4/2009 | Ooida | |
| 2009/0114218 A1 | 5/2009 | Veatch | |
| 2009/0114742 A1 | 5/2009 | Collins, Jr. | |
| 2009/0118243 A1 | 5/2009 | Gjorstrup | |
| 2009/0134235 A1 | 5/2009 | Ivri | |
| 2009/0167812 A1 | 7/2009 | Asai et al. | |
| 2009/0192443 A1 | 7/2009 | Collins, Jr. | |
| 2009/0202862 A1 | 8/2009 | Chen et al. | |
| 2009/0212133 A1 | 8/2009 | Collins, Jr. | |
| 2009/0235925 A1 | 9/2009 | Power et al. | |

(56) References Cited

U.S. PATENT DOCUMENTS

| | | |
|---|---|---|
| 2009/0270752 A1 | 10/2009 | Coifman |
| 2009/0272818 A1 | 11/2009 | Valpey, III et al. |
| 2009/0314292 A1 | 12/2009 | Overfield et al. |
| 2009/0317496 A1 | 12/2009 | Park et al. |
| 2010/0037894 A1 | 2/2010 | Rouse et al. |
| 2010/0078013 A1 | 4/2010 | Power et al. |
| 2010/0089395 A1 | 4/2010 | Power et al. |
| 2010/0140291 A1* | 6/2010 | Hailes ............... B05B 17/0669 239/102.1 |
| 2010/0156995 A1 | 6/2010 | Kanda et al. |
| 2010/0181387 A1 | 7/2010 | Zaffaroni et al. |
| 2010/0222752 A1 | 9/2010 | Collins, Jr. et al. |
| 2010/0273895 A1 | 10/2010 | Stinchcomb et al. |
| 2010/0282247 A1 | 11/2010 | Kadrichu et al. |
| 2011/0094523 A1 | 4/2011 | Thorens et al. |
| 2011/0108025 A1 | 5/2011 | Fink et al. |
| 2011/0114090 A1 | 5/2011 | Piper |
| 2011/0230820 A1 | 9/2011 | Lillis et al. |
| 2011/0253139 A1 | 10/2011 | Guthrie et al. |
| 2011/0253140 A1 | 10/2011 | Smyth et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0092416 A1 | 4/2012 | Platt et al. |
| 2012/0266878 A1 | 10/2012 | Watanabe et al. |
| 2012/0291781 A1 | 11/2012 | Kaufmann et al. |
| 2013/0064777 A1 | 3/2013 | Tamarkin et al. |
| 2013/0079732 A1 | 3/2013 | Burt et al. |
| 2013/0150812 A1 | 6/2013 | Hunter et al. |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0284165 A1 | 10/2013 | Krimsky |
| 2013/0299607 A1 | 11/2013 | Wilkerson et al. |
| 2013/0319404 A1 | 12/2013 | Feriani et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0230817 A1 | 8/2014 | Richardson |
| 2014/0231538 A1 | 8/2014 | Tabata et al. |
| 2014/0283859 A1 | 9/2014 | Minskoff et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136129 A1 | 5/2015 | Mehadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0273165 A1 | 10/2015 | Hadash |
| 2015/0283339 A1 | 10/2015 | Mahadevan et al. |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0082208 A1 | 3/2016 | Ballam et al. |
| 2016/0106341 A1 | 4/2016 | Adam et al. |
| 2016/0129182 A1 | 5/2016 | Schuster et al. |
| 2016/0166768 A1 | 6/2016 | Edwards et al. |
| 2016/0213864 A1 | 7/2016 | Eilat et al. |
| 2016/0213866 A1 | 7/2016 | Tan |
| 2016/0245830 A1 | 8/2016 | Mace et al. |
| 2016/0250426 A1* | 9/2016 | Morrison .......... A61M 15/0085 128/200.16 |
| 2016/0300590 A1 | 10/2016 | Chen et al. |
| 2016/0310982 A1 | 10/2016 | Von Hollen |
| 2016/0325055 A1 | 11/2016 | Cameron |
| 2016/0354557 A1 | 12/2016 | McPherson Allnutt et al. |
| 2017/0007449 A1 | 1/2017 | Nielsen |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1 | 11/2017 | Hemy et al. |
| 2018/0021528 A1 | 1/2018 | Hsieh et al. |
| 2018/0021530 A1 | 1/2018 | Fink et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0209790 A1* | 7/2019 | Maeda ..................... B06B 3/02 |
| 2019/0224426 A1 | 7/2019 | Farina et al. |
| 2019/0343793 A1 | 11/2019 | Gunther et al. |
| 2019/0358420 A1 | 11/2019 | Hunter et al. |
| 2020/0060346 A1 | 2/2020 | Danek |
| 2020/0147325 A1 | 5/2020 | Wilson et al. |
| 2020/0230329 A1 | 7/2020 | Danek |
| 2020/0246556 A1 | 8/2020 | Osoegawa et al. |
| 2020/0276398 A1 | 9/2020 | Hebrank et al. |
| 2020/0289770 A1 | 9/2020 | Hebrank et al. |
| 2020/0315842 A1 | 10/2020 | Palanker et al. |
| 2020/0345588 A1 | 11/2020 | Merrell et al. |
| 2020/0353186 A1 | 11/2020 | Hebrank et al. |
| 2021/0022406 A1* | 1/2021 | Minami ................ F24H 15/219 |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |
| 2022/0211304 A1 | 7/2022 | Dellimore et al. |
| 2022/0296823 A1 | 9/2022 | Hebrank et al. |
| 2023/0201486 A1 | 6/2023 | Tang et al. |
| 2023/0356253 A1 | 11/2023 | Scoggin et al. |

FOREIGN PATENT DOCUMENTS

| | | |
|---|---|---|
| CH | 715947 | 11/2020 |
| CN | 1788806 | 6/2006 |
| CN | 104511072 | 4/2015 |
| CN | 204995458 | 1/2016 |
| CN | 205019058 | 2/2016 |
| CN | 112617297 | 4/2021 |
| CN | 1124247016 | 3/2022 |
| EP | 0084458 | 7/1983 |
| EP | 0923957 | 10/2001 |
| EP | 2724741 | 4/2014 |
| EP | 3127616 | 2/2017 |
| JP | H11-042219 | 2/1999 |
| JP | 2003-265994 | 9/2003 |
| JP | 2006-68508 | 3/2006 |
| KR | 10-2019-122453 | 10/2019 |
| WO | WO 93/12823 | 7/1993 |
| WO | WO 96/09846 | 4/1996 |
| WO | WO 96/14163 | 5/1996 |
| WO | WO 98/48873 | 11/1998 |
| WO | WO 00/10634 | 3/2000 |
| WO | WO 00/47335 | 8/2000 |
| WO | WO 00/50112 | 8/2000 |
| WO | WO 01/85244 | 11/2001 |
| WO | WO 01/87378 | 11/2001 |
| WO | WO 02/068128 | 9/2002 |

(56) References Cited

FOREIGN PATENT DOCUMENTS

| | | |
|---|---|---|
| WO | WO 03/020349 | 3/2003 |
| WO | WO 03/059413 | 7/2003 |
| WO | WO 2004/078025 | 9/2004 |
| WO | WO 2006/013952 | 2/2006 |
| WO | WO 2006/083014 | 8/2006 |
| WO | WO 2006/102345 | 9/2006 |
| WO | WO 2006/108558 | 10/2006 |
| WO | WO 2007/107160 | 9/2007 |
| WO | WO 2008/056986 | 5/2008 |
| WO | WO 2008/058941 | 5/2008 |
| WO | WO 2008/106616 | 9/2008 |
| WO | WO 2008/116165 | 9/2008 |
| WO | WO 2009/012371 | 1/2009 |
| WO | WO 2009/0099438 | 8/2009 |
| WO | WO 2009/111612 | 9/2009 |
| WO | WO 2010/065452 | 6/2010 |
| WO | WO 2010/065616 | 6/2010 |
| WO | WO 2011/042212 | 4/2011 |
| WO | WO 2011/083377 | 7/2011 |
| WO | WO 2011/091268 | 7/2011 |
| WO | WO 2011/163272 | 12/2011 |
| WO | WO 2012/026963 | 3/2012 |
| WO | WO 2013/098334 | 7/2013 |
| WO | WO 2013/132056 | 9/2013 |
| WO | WO 2013/158352 | 10/2013 |
| WO | WO 2013/158967 | 10/2013 |
| WO | WO 2013/173321 | 11/2013 |
| WO | WO 2014/147550 | 9/2014 |
| WO | WO 2015/004554 | 1/2015 |
| WO | WO 2015/106150 | 7/2015 |
| WO | WO 2015/136529 | 9/2015 |
| WO | WO 2015/176033 | 11/2015 |
| WO | WO 2015/191478 | 12/2015 |
| WO | WO 2015/191481 | 12/2015 |
| WO | WO 2016/001923 | 1/2016 |
| WO | WO 2016/001924 | 1/2016 |
| WO | WO 2016/003738 | 1/2016 |
| WO | WO 2016/030521 | 3/2016 |
| WO | WO 2017/015303 | 1/2017 |
| WO | WO 2017/056103 | 4/2017 |
| WO | WO 2018/213834 | 11/2018 |
| WO | WO 2019/071008 | 4/2019 |
| WO | WO 2019/079461 | 4/2019 |
| WO | WO 2019/136437 | 7/2019 |
| WO | WO 2019/219865 | 11/2019 |
| WO | WO 2019/219873 | 11/2019 |
| WO | WO 2020/072478 | 4/2020 |
| WO | WO 2020/141424 | 7/2020 |
| WO | WO 2020/154497 | 7/2020 |
| WO | WO 2020/227717 | 11/2020 |
| WO | WO-2020227717 A1 * 11/2020 .......... A61M 11/005 | |
| WO | WO 2020/264501 | 12/2020 |
| WO | WO 2021/090135 | 5/2021 |
| WO | WO 2021/203038 | 10/2021 |
| WO | WO 2022/051496 | 3/2022 |
| WO | WO 2022/226407 | 10/2022 |
| WO | WO 2022/271848 | 12/2022 |
| WO | WO 2023/278551 | 1/2023 |
| WO | WO 2023/064477 | 4/2023 |
| WO | WO 2023/091637 | 5/2023 |

OTHER PUBLICATIONS

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnoea in patients with COPD," *Respiratory Medicine*, 2011, 105, 316-312.

Steller, "Microcontroller Based Diagnostic Smart Inhaler," University of Cincinnati, Dec. 7, 2014, 63 pages.

Carvalho et al., "The function and performance of aqueous aerosol devices for inhalation therapy," Journal of Pharmacy and Pharmacology, vol. 68, No. 5, Apr. 8, 2016, pp. 556-578.

Pneuma Respiratory, Digitally breath-actuated inhaler device with precision droplet ejector technology and digital dose confidence. Available on Mar. 18, 2017 [retrieved on Jun. 30, 2017]. Retrieved from the Internet: URL: https://pneumarespiratory.com/. 3 pp.

Azzopardi, "Sauter Mean Diameter" Sep. 30, 2012, 4 pages, https://web.archive.org/web/20120930225842/http://www.termopedia.com/content/1108, retrieved May 26, 2014.

Ultrasonic Vibrating member catalog—Emerson. Catalog—Ultrasonic Vibrating member (2014). Available at: https://www.emerson.com/documents/automation/catalog-ultrasonic-vibratingmember-branson-en-us-160126.pdf. (Accessed:Aug. 9, 2023).

Lin, J. & Lin, S. "Study on a large-scale three-dimensional ultrasonic plastic welding vibration system based on a quasi-periodic phononic crystal structure," Crystals 2020, 10, 21, MDPI, 18 pages.

Industrial resonators Available at: http://www.krell-engineering.com/fea/industr/industrial_resonators.htm, accessed Aug. 9, 2023, 7 pages.

Gonzalez-Rothi et al, "Pulmonary Delivery of Liposome-Encapsulated Drugs in Asthma Therapy," Clin Immunother 4, 331-337 (1995).

Tronde et al., "Pulmonary Absorption Rate and Bioavailability of Drigs In Vivo in Rats: Structure-Absorption Relationships and Physicochemical Profiling of Inhaled Drugs," J Pharm Sci, 92 (2003) 1216-1233.

Law et al, "Atomization of High-Viscosity Fluids for Aromatherapy Using Micro-heaters for Heterogeneous Bubble Nucleation," Scientific Reports vol. 7, Article No. 40289 (2017), 14 pages.

\* cited by examiner

SMALL STEP SIZE AND HIGH RESOLUTION AEROSOL GENERATION SYSTEM AND METHOD

CROSS-REFERENCE TO RELATED APPLICATIONS

This application claims the benefit of priority of U.S. Provisional Patent Application No. 63/390,209 filed Jul. 18, 2022, which is incorporated herein by reference in its entirety.

FIELD

The present disclosure relates generally to aerosol generation devices that include a vibrating transducer, such as piezoelectric transducer. Examples include droplet delivery devices that deliver fluids that are inhaled into the mouth, throat, nose, and/or lungs.

BACKGROUND

Aerosol generation devices may include a vibrating transducer, such as a piezoelectric transducer, to create aerosolized droplets for a variety of applications. Some aerosol generation devices include droplet delivery systems directed to both therapeutic and non-therapeutic uses. Current droplet delivery systems include a variety of inhaler type systems. Some examples are metered dose inhalers (MDI), pressurized metered dose inhalers (p-MDI), pneumatic devices, and ultrasonic-driven devices. Such droplet delivery systems are directed to both therapeutic and non-therapeutic uses and may include mouthpieces and nosepieces to provide for inhalation of the fluid droplets.

SUMMARY OF THE INVENTION

In one embodiment of the invention, an aerosol generation device comprises: a reservoir configured to supply a volume of fluid; a mesh in fluid communication with the reservoir and operably coupled to a vibrating member; an electronic transducer coupled to the vibrating member, the electronic transducer configured to operate at a first frequency that oscillates the vibrating member to generate an ejected stream of droplets through the mesh; and a circuit board or microcontroller providing a plurality of tuning signal waves to the electronic transducer during a tuning mode and measuring a current provided at a constant voltage; and wherein the circuit board or microcontroller determines a detected resonance frequency at which a highest current draw is detected and selects the detected resonance frequency at the highest current draw to drive the electronic transducer. In embodiments, the electronic transducer is a piezoelectric transducer.

In a further embodiment, an aerosol generation device of the invention includes a membrane coupled between the vibrating member and mesh.

In a further embodiment, an aerosol generation device of the invention is a droplet delivery device including a mouthpiece or nosepiece configured for inhalation.

In a further embodiment, an aerosol generation device of the invention includes the detected resonance frequency having a lower step size than the first frequency.

In another embodiment, an aerosol generation device of the invention includes a piezoelectric transducer operable to generate a droplet from fluid in the device; an ejector mechanism coupled to the piezoelectric transducer and configured to receive the fluid; and an auto-tuning circuit or microcontroller configured to adjust a first driving frequency of the piezoelectric transducer to a second driving frequency of the piezoelectric transducer to compensate for resonant frequency drift.

The aerosol generation in a further embodiment further includes the auto-tuning or microcontroller configured to conduct current analysis on the piezoelectric transducer during operation and providing adjustment to the second driving frequency based on measurement of a highest current draw across various frequencies tested during the current analysis.

In embodiments of the invention, the ejector mechanism includes an aperture plate coupled to the piezoelectric transducer.

In further embodiments, the second driving frequency has a lower step size than the first driving frequency.

In another embodiment of the invention, an aerosol generation device includes a reservoir configured to supply a volume of fluid to a mesh of an ejector mechanism, an electronic transducer operable to operate at a first frequency based upon a signal wave generated by a circuit, wherein the signal wave has a step size smaller than about 200 Hz, and wherein the transducer is operable to vibrate a mesh and generate at least one droplet from fluid supplied by the reservoir to the mesh. a microcontroller or circuit that provides a plurality of signal waves to the electronic transducer during a tuning mode and measuring a current provided at a constant voltage, determines a detected resonance frequency at which a highest current draw is detected from providing the plurality of signal waves, and selects the detected resonance frequency to drive the electronic transducer.

In embodiments of the invention, the electronic transducer is a piezoelectric transducer.

The aerosol generation device in various embodiments is a droplet delivery device including a mouthpiece or nosepiece configured for inhalation.

In embodiments, an aerosol generation device further includes a membrane coupled between the piezoelectric transducer and the aperture plate.

BRIEF DESCRIPTION OF THE DRAWINGS

The novel features of the disclosure are set forth with particularity in the appended claims. A better understanding of the features and advantages of the present inventive concept will be obtained by reference to the following detailed description that sets forth illustrative examples, in which the principles of the disclosure are utilized, and the accompanying drawings of which:

DETAILED DESCRIPTION

Figure 1:
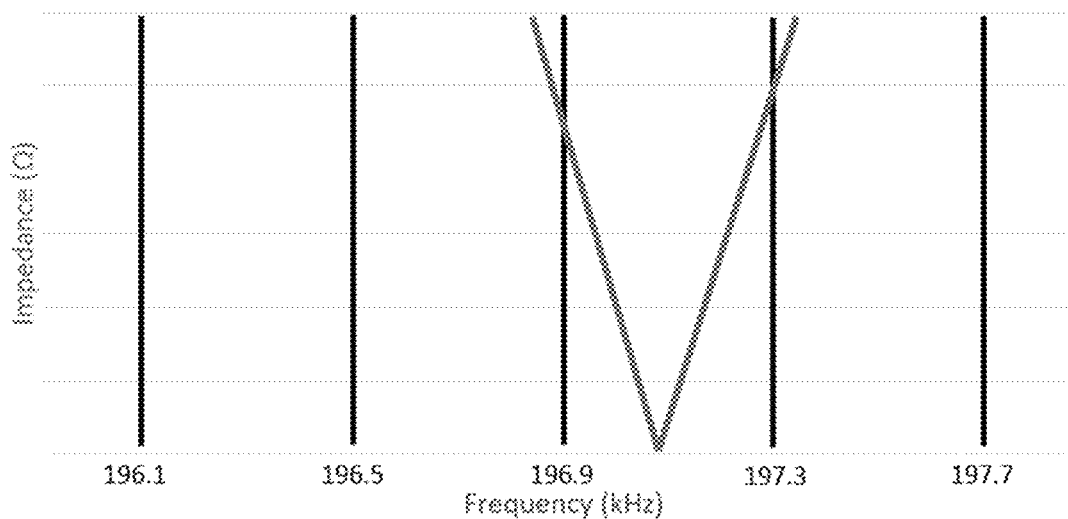
FIG. 1 illustrates an example graph of driving a piezoelectric transducer at two frequencies to select the one with the highest current in an embodiment of the invention.
Figure 1:
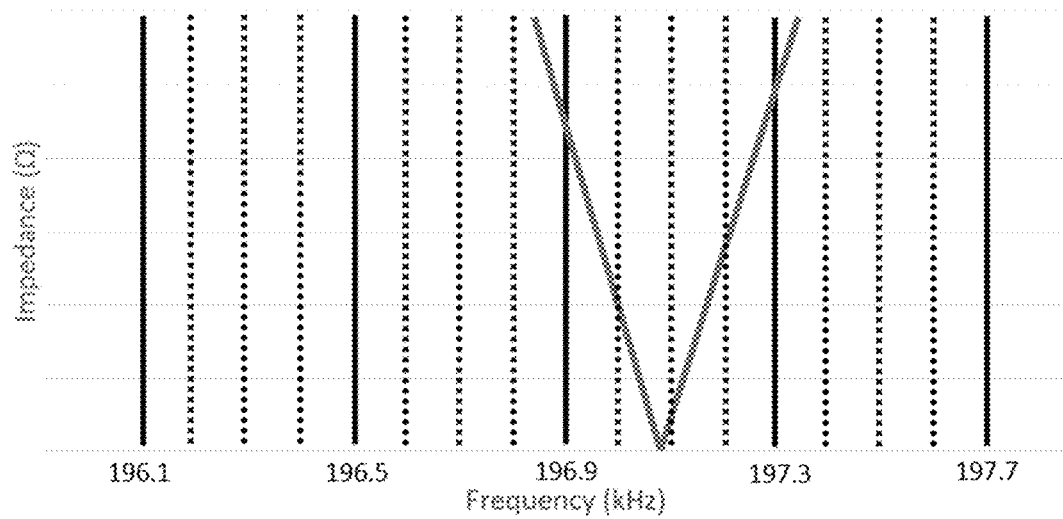
Figure 2:
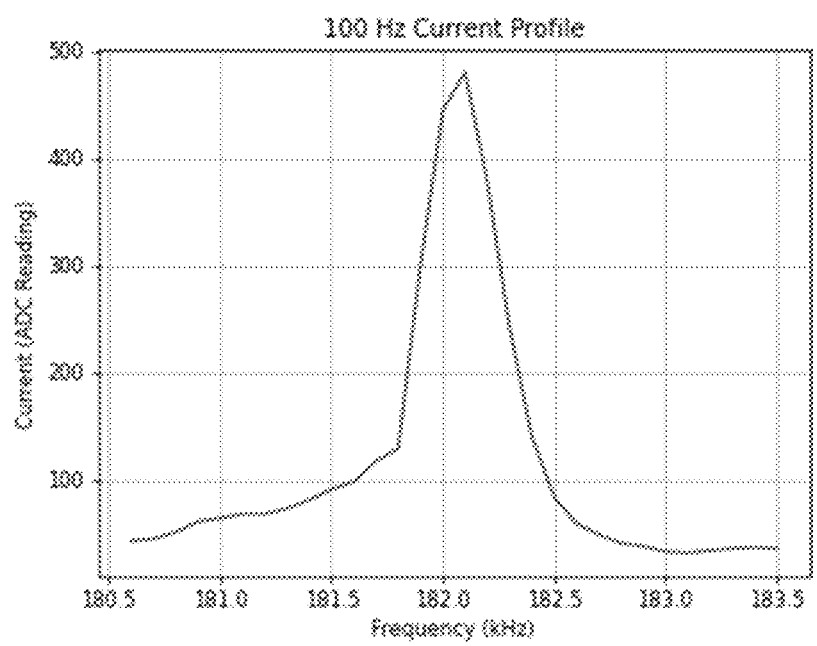
FIG. 2 illustrates an example graph of current vs. frequency for 100 Hz current profile in an embodiment of the present invention.
Figure 3:
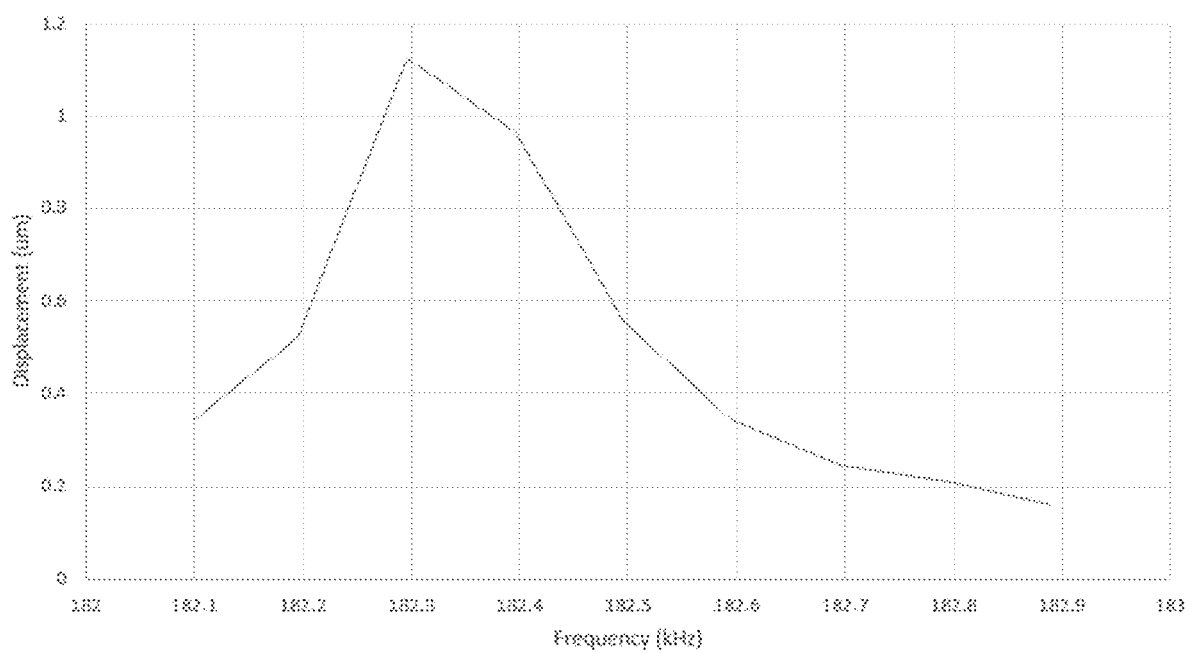
FIG. 3 illustrates an example graph of displacement of a piezoelectric transducer at different frequencies in an embodiment of the present invention.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited only those elements but can include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term substantially, as used herein, is defined to be essentially conforming to the particular dimension, shape or other word that substantially modifies, such that the component need not be exact. For example, substantially cylindrical means that the object resembles a cylinder, but can have one or more deviations from a true cylinder.

The term "coupled" is defined as connected, whether directly or indirectly through intervening components, and is not necessarily limited to physical connections. The connection can be such that the objects are permanently connected or releasably connected. The term "comprising" means "including, but not necessarily limited to"; it specifically indicates open-ended inclusion or membership in a so-described combination, group, series and the like.

Droplet delivery devices include an ejector mechanism with a mesh, aperture plates and like substrates having desirably sized holes and producing desirable surface contact angle that creates droplets from liquid passing through the mesh when a powered transducer acts on the liquid and ejector mechanism. In some devices a membrane may be oscillated by a powered transducer to push the liquid through the mesh and create droplets ("push mode"), while in other devices a transducer can be coupled directly to oscillate the mesh to create droplets. Examples of devices including such ejector mechanisms with substrates having apertures are described in U.S. Patent Application Pub. No. US2022/0401661 entitled "DELIVERY DEVICE WITH PUSH EJECTION" published Dec. 22, 2022, International Publication Number WO 2020/264501 entitled "DELIVERY OF SMALL DROPLETS TO THE RESPIRATORY SYSTEM VIA ELECTRONIC BREATH ACTUATED DROPLET DELIVERY DEVICE" published Dec. 30, 2020, and International Publication Number WO 2020/227717 entitled "ULTRASONIC BREATH ACTUATED RESPIRATORY DROPLET DELIVERY DEVICE AND METHODS OF USE" published Nov. 12, 2020, all of which are herein incorporated by reference in their entirety, including incorporation of such publications and patent applications as are cited and incorporated by reference or relied upon in the referenced disclosures.

The present technology can be implemented in different configurations. In one example, the present technology implements a vibrating member, such as a piezoelectric transducer with a horn (that may also be coupled to a membrane as in "push mode" technology), that pushes liquid through a fixed mesh to generate droplets. The configuration of the horn and mesh and other components can vary, but at least one example is presented herein. In another example, the present technology implements a vibrating mesh operable to move in and out of a liquid, thereby generating a jet of liquid, exiting the mesh, that turns into a droplet.

In one example, the present technology implements a piezoelectric transducer to eject a liquid through a mesh. In at least one example, the ejection of liquid results in the formation of at least one droplet.

The present technology implements a circuit having one or more clocks that can have a clock frequency. In some embodiments, the clock(s) can be further refined as needed using additional circuitry. A piezoelectric transducer has a specific resonance frequency that it runs at to have the maximum amplitude thereby maximizing the liquid ejection. Furthermore, the transducer is operable to provide the most consistent amount of liquid ejected. The circuit board is operable to generate a signal wave that is sent to the piezoelectric transducer. The signal wave is operable to drive the piezoelectric transducer to operate in a particular way. The circuit board is operable to generate a particular frequency step size to generate the signal wave. The step size is determined by the clock frequency of the circuit. In at least one example, the clock frequency can come from a microcontroller. In another example, the clock frequency can come from the circuit board. The present technology implements a high clock frequency to provide enhanced resolution in the step size. For example, the present technology can decrease an existing step size from about 400 Hz to 1 Hz. This decrease in step size allows the applied frequency to be closer to the piezoelectric transducer assembly resonance frequency which maximizes the mass ejection. The present technology can implement a small step size for increased performance.

The present technology is also operable to find and drive the piezoelectric transducer at its resonance frequency. In manufacturing and selecting different piezoelectric transducers, the resonance frequency might differ across a production run or further from one production run to another. Additionally, there are other factors that change a piezoelectric transducer's resonance frequency. For example, the resonance frequency can be changed based on the temperature of the piezoelectric transducer. Additionally, as the piezoelectric device vibrates during operation, the temperature of the piezoelectric transducer changes. Thus, during operation and ejection of the liquid, the piezoelectric transducer experiences a change in resonance frequency. Additional factors that can change the resonance frequency include the amount of liquid being ejected and type of liquid.

Electrical current analysis can compensate for the decrease in resonant frequency of a piezoelectric transducer during actuation due to rising temperature. This is done by doing a refresh at specific time intervals (e.g. 1 ms, 10 ms, 100 ms, 250 ms, 500 ms, 1000 ms). The refresh monitors the electrical current of the piezoelectric transducer actuation at a range of frequencies near the previously found resonant frequency. The driving frequency is set to a new frequency to compensate for the resonant frequency drift. It can be assumed that the resonant frequency will only decrease during actuation, so only frequencies below the initial resonant frequency should have to be monitored to effectively compensate for the resonant frequency shift.

The present technology implements an auto-tune feature, whereby the circuit tries a plurality of frequencies and selects the frequency closest to the resonance frequency. In order to determine the resonance frequency, the circuit can use sensors to determine the resonance frequency. For example, the resonance frequency can be defined as the point at which impedance is the lowest. The circuit can also use a fixed voltage to drive the piezoelectric device and detect when the current is at the highest across multiple frequencies. The determination of when the current is at the highest for a particular frequency will provide the resonance frequency. For example, the auto tune mode can drive the piezoelectric transducer at a plurality of frequencies and measure the current at each frequency. The auto tune feature can then select the one with the highest current. An example of the change in driving frequency is illustrated in FIG. 1. The device can be configured to auto-tune at a predetermined time and/or based on a temperature measurement of the piezoelectric transducer. The auto-tune allows the ejection of liquid to be made at the resonance frequency thereby maximizing the amount of liquid ejected and providing the most consistent ejection.

Figure 4:
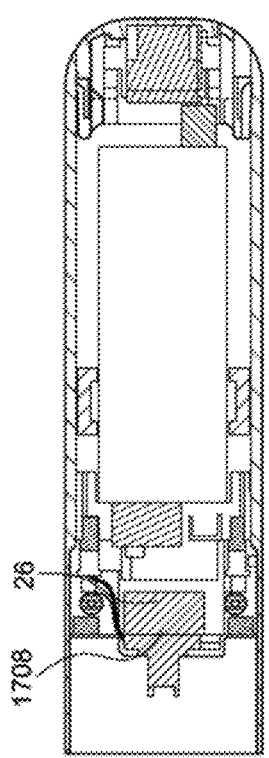
FIG. 4 is a cross-sectional view of major components of a droplet delivery device in accordance with an embodiment of the disclosure.
Figure 4:
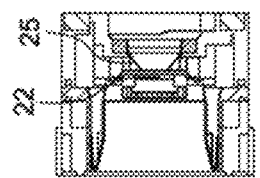
Figure 4:
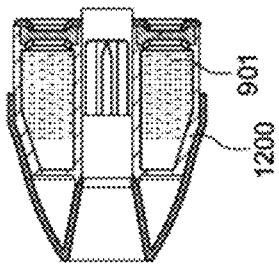
Figure 5:
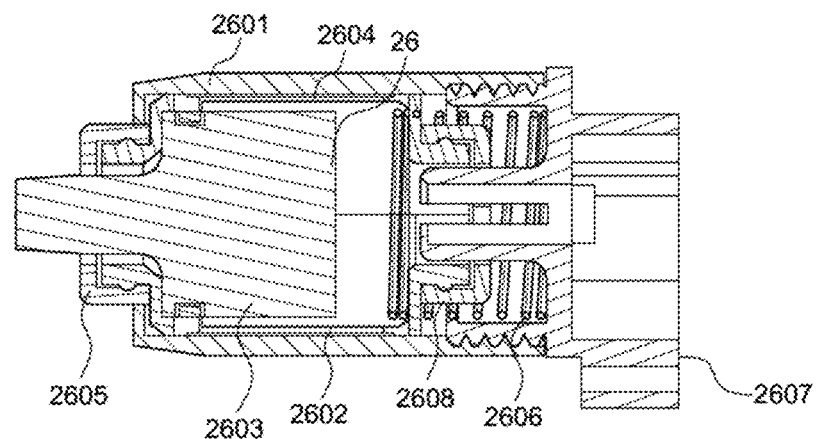
FIG. 5 illustrates a cross-sectional view of a vibrating member enclosure of a droplet delivery device utilizing membrane-driven aerosolization in accordance with one embodiment of the disclosure.
Figure 6A:
FIG. 6A illustrates a side plan view of an exemplary aperture plate and annulus ring, in accordance with an embodiment of the disclosure.
Figure 6B:
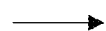
FIG. 6B illustrates a top plan view of an exemplary aperture plate and annulus ring, in accordance with an embodiment of the disclosure.
Figure 6C:
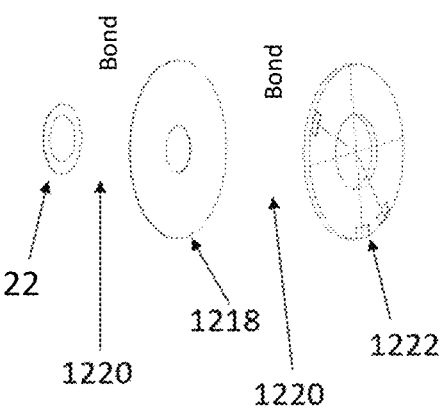
FIG. 6C illustrates a cross-section of an exemplary aperture plate and annulus ring configuration, in accordance with an embodiment of the disclosure.

The above description applies to a configuration of the present technology that implements a piezoelectric transducer, horn, and liquid assembly, which are further described with reference to FIGS. 4 and 5. In other examples, the present technology can implement a piezoelectric transducer, mesh, and liquid assembly. The present technology implements controller, circuit board, clock, and/or microcontroller having the above features to drive the piezoelectric transducer, which then causes the mesh to vibrate. As the mesh vibrates, the fluid is expelled through the mesh in a jet. The jet turns into a droplet. Further details regarding this configuration are presented below with reference to FIGS. 6A-6C.

FIG. 1 illustrates two different step sizes that are used to drive the frequency selection. The lower resolution has a frequency variation of about 400 Hz. The higher resolution has a frequency variation of about 100 Hz. Measuring the impedance allows the resonance frequency to be determined, and it can be more closely approximated by the higher resolution. Thus, implementing the smaller step size in regard to frequency generation allows for the resonance frequency to be better approximated and matched to generate the best signal possible to control the piezoelectric transducer. In embodiments to the invention, the smaller step size is lower than about 200 Hz, and preferably at around 100 Hz, and even to a lower step size of 1 Hz in certain embodiment, such that a more precise step size can more accurately determine the resonance frequency of an electronic/piezoelectric transducer. In the described embodiment with reference to FIG. 1, the resonance frequency of a piezoelectric transducer is determined by actuating the transducer with several different frequencies and analyzing the current draw at each frequency in the system, and is not technically a full impedance analysis.

With reference to FIG. 2, the 100 Hz current profile graph shows data that was extracted from a microcontroller of an aerosol generation device of the invention with a piezoelectric transducer to verify that the resonant frequency is determinable, i.e., the frequency chosen is the peak current found in the illustrated data.

The graph of FIG. 3 illustrates piezoelectric transducer displacement at different frequencies. The data was acquired with a laser vibrometer (the MV-H™ Series vibrometer from OmniSensing Photonics, LLC (Columbia, MD)) and shows how precise frequency step sizes of 100 Hz can affect the mechanical displacement of the piezoelectric transducer. Peak to peak voltage for the measured data of FIG. 3 was about 5 V.

An example device according to the present technology can be described as follows and illustrated in FIG. 4. A droplet delivery device having a membrane that cooperates with a mesh further includes a PZT-based ultrasonic transducer coupled to a vibrating member having a tip portion made of at least one of Grade 5 titanium alloy, Grade 23 titanium alloy, and about 99% or higher purity titanium. In certain embodiments, the vibrating member's tip includes a sputtered on outer layer of and about 99% or higher purity titanium providing a smooth tip surface configured to contact an underlying bottom surface of the membrane that is opposite an exterior top surface of the membrane positioned nearest the mesh to help reduce wear of the membrane and increase the longevity and operation consistency of the membrane (and also possibly vibrating member's tip portion). The transducer can be configured to have the desired higher frequency as described above. A vibrating member 1708 and transducer 26 work in conjunction with a membrane 25 and mesh 22 to aerosolize fluid 901, which is held in a reservoir 1200 and supplied to the mesh 22 using various methods (e.g., wick material, hydrophilic coatings, capillary action, etc.). Preferably the vibrating member is coupled to the transducer, such as by bonding (e.g., adhesives and the like), welding, gluing, physical connections (e.g., brackets and other mechanical connectors), and the like. The transducer and vibrating member interact with the membrane to push fluid through the mesh. As illustrated and described in various embodiments, the membrane may in some cases contact the mesh while also "pushing" fluid through holes in the mesh and may in other cases be separated without contacting the mesh to push liquid through holes in the mesh. The transducer may comprise one or more of a variety of materials (e.g., PZT, etc.). In certain embodiments the transducer is made of lead-free piezoelectric materials to avoid creation of unwanted or toxic materials in a droplet delivery device intended for human inhalation. The vibrating member may be made of one or more of a variety of different materials (e.g., titanium, etc.). The mesh may be one or more of a variety of materials (e.g., palladium nickel, polyimide, etc.). After the fluid is pushed through the mesh, a droplet spray is formed and ejected through a mouthpiece port, carried by entrained air.

As shown in FIG. 5, the main body of a second example contains the vibrating member and transducer assembly 2603. The vibrating member and transducer assembly 2603 is encased by a vibrating member front cover 2602 and vibrating member rear cover 2604. The covers 2602, 2604 are held together by circular caps called the front and rear vibrating member cover holders 2605, 2608. The encased vibrating member is then put into the vibrating member enclosure 2601, followed by the vibrating member assembly spring 2606, and finally seated into the vibrating member device bracket 2607. The vibrating member enclosure allows the spring to press the vibrating member and transducer assembly to the membrane.

FIGS. 6A-6C illustrate an aperture plate assembly 1210 that includes an aperture plate 22 (e.g., palladium-nickel) supported by a stainless-steel annulus 1218. The aperture plate is welded or bonded 1220 to the stainless-steel annulus 1218, thereby together allowing a thicker support material which is much less expensive than aperture plate material alone e.g., palladium-nickel. The stainless steel and aperture plate are bonded 1220 to the piezo-electric material 1222 wherein all the components form the aperture plate assembly 1210.

While the invention has been described with reference to exemplary embodiments, it will be understood by those skilled in the art that various changes may be made, and equivalents may be substituted for elements thereof without departing from the scope of the invention. In addition, many modifications may be made to adapt a particular situation or material to the teachings without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. An aerosol generation device comprising:
   a piezoelectric transducer operable to generate a droplet from fluid in the device, wherein the piezoelectric transducer has an initial resonant frequency;
   an ejector mechanism coupled to the piezoelectric transducer and configured to receive the fluid; and
   an auto-tuning circuit or microcontroller configured to provide during operation of the piezoelectric transducer a plurality of tuning signal waves based on measurement of temperature of the piezoelectric transducer, wherein the frequency of a tuning signal wave is only lower than the initial resonant frequency during operation of the piezoelectric transducer, and wherein the frequency difference between consecutive tuning signal waves is from 1 Hz to 200 Hz to adjust a first driving frequency of the piezoelectric transducer to a second driving frequency of the piezoelectric transducer to compensate for resonant frequency drift.

2. The aerosol generation device of claim 1, further comprising the auto-tuning circuit or microcontroller configured to conduct current analysis on the piezoelectric transducer during operation and providing adjustment to the second driving frequency based on measurement of a highest current draw across various frequencies tested during the current analysis.

3. The aerosol generation device of claim 2, wherein the ejector mechanism includes an aperture plate coupled to the piezoelectric transducer.

4. The aerosol generation device of claim 3, wherein the aerosol generation device is a droplet delivery device including a mouthpiece or nosepiece configured for inhalation.

5. The droplet delivery device of claim 4, wherein the second driving frequency has a lower step size than the first driving frequency.

6. The aerosol generation device of claim 3, further comprising a membrane coupled between the piezoelectric transducer and the aperture plate.

7. The aerosol generation device of claim 1, wherein the ejector mechanism includes an aperture plate coupled to the piezoelectric transducer.

8. The aerosol generation device of claim 7, further comprising a membrane coupled between the piezoelectric transducer and the aperture plate.

9. The aerosol generation device of claim 8, wherein the aerosol generation device is a droplet delivery device including a mouthpiece or nosepiece configured for inhalation.

10. The aerosol generation device of claim 1, further comprising the auto-tuning circuit or microcontroller providing the plurality of tuning signal waves during operation of the piezoelectric transducer at a predetermined time interval.

11. The aerosol generation device of claim 10, wherein the predetermined time interval is from 1 ms to 1000 ms during operation of the piezoelectric transducer.

12. An aerosol generation device comprising:
    a reservoir configured to supply a volume of fluid to a mesh of an ejector mechanism;
    an electronic transducer operable to operate at a first frequency based upon a signal wave generated by a microcontroller or circuit, wherein the signal wave has a step size smaller than about 200 Hz, and wherein the transducer is operable to vibrate the mesh and generate at least one droplet from fluid supplied by the reservoir to the mesh;
    the microcontroller or circuit provides a plurality of signal waves to the electronic transducer during a tuning mode initiated based on measurement of temperature of the electronic transducer and measures a current provided at a constant voltage, determines a detected resonance frequency at which a highest current draw is detected from providing the plurality of signal waves, and selects the detected resonance frequency to drive the electronic transducer.

13. The aerosol generation device of claim 12, wherein the electronic transducer is a piezoelectric transducer.

14. The aerosol generation device of claim 13, wherein the aerosol generation device is a droplet delivery device including a mouthpiece or nosepiece configured for inhalation.

15. The aerosol generation device of claim 14, further comprising a membrane coupled between the piezoelectric transducer and the aperture plate.

16. The aerosol generation device of claim 13, further comprising a membrane coupled between the piezoelectric transducer and the mesh.

17. The aerosol generation device of claim 12, further comprising a membrane coupled between the piezoelectric transducer and the mesh.

18. The aerosol generation device of claim 12, further comprising the microcontroller or circuit providing the plurality of signal waves during the tuning mode at a predetermined time interval.

19. The aerosol generation device of claim 18, wherein the predetermined time interval is from 1 ms to 1000 ms during operation of the electronic transducer.

* * * * *